United States Patent
von Bohl et al.

(10) Patent No.: US 11,959,070 B2
(45) Date of Patent: Apr. 16, 2024

(54) PROCESS FOR ISOLATING NUCLEIC ACIDS FROM SAMPLE MATERIALS

(71) Applicant: Axagarius GmbH & Co. KG, Dueren (DE)

(72) Inventors: Andreas von Bohl, Aachen (DE); Yvonne Schuell, Merzenich (DE)

(73) Assignee: Axagarius GmbH & Co. KG, Dueren (DE)

( * ) Notice: Subject to any disclaimer, the term of this patent is extended or adjusted under 35 U.S.C. 154(b) by 450 days.

(21) Appl. No.: 16/830,745

(22) Filed: Mar. 26, 2020

(65) Prior Publication Data

US 2020/0308570 A1 Oct. 1, 2020

(30) Foreign Application Priority Data

Mar. 28, 2019 (DE) .................. 10 2019 108 087.8

(51) Int. Cl.
*C12N 15/10* (2006.01)

(52) U.S. Cl.
CPC ................................ *C12N 15/1013* (2013.01)

(58) Field of Classification Search
None
See application file for complete search history.

(56) References Cited

U.S. PATENT DOCUMENTS

| 10,214,739 | B2 | 2/2019 | Kirsch |
| 2002/0192667 | A1 | 12/2002 | Kojima et al. |
| 2017/0121702 | A1 | 5/2017 | Kirsch |

FOREIGN PATENT DOCUMENTS

| EP | 1502951 A1 | 2/2005 |
| EP | 1524317 A1 | 4/2005 |
| EP | 1526176 A2 | 4/2005 |
| EP | 1626085 A1 | 2/2006 |
| EP | 1354036 B1 | 5/2010 |
| EP | 2322613 A1 | 5/2011 |
| EP | 2137309 B1 | 7/2013 |

OTHER PUBLICATIONS

Gaspar, Imre et al. "Terminal Deoxynucleotidyl Transferase Mediated Production of Labeled Probes for Single-molecule FISH or RNA Capture." Bio-protocol vol. 8,5 e2750. Mar. 5, 2018, doi: 10.21769/BioProtoc.2750.*
Min, Ji Hyun, et al. "Isolation of DNA using magnetic nanoparticles coated with dimercaptosuccinic acid." Analytical biochemistry 447 (2014): 114-118.*
Rittich, Bohuslav, et al. "Isolation of microbial DNA by newly designed magnetic particles." Colloids and Surfaces B: Biointerfaces 52.2 (2006): 143-148.*
European Search Report dated Jun. 24, 2020 in corresponding application 20164898.7-1118.

* cited by examiner

*Primary Examiner* — Patrick T Lewis
(74) *Attorney, Agent, or Firm* — Norris Mclaughlin, P.A.

(57) ABSTRACT

The invention relates to a process for isolating nucleic acids, such as DNA and RNA, using a non-alcoholic and non-chaotropic binding solution, and to the binding solutions and kits suitable for such a process.

22 Claims, 2 Drawing Sheets

PROCESS FOR ISOLATING NUCLEIC ACIDS FROM SAMPLE MATERIALS

PRIORITY

This application claims foreign priority benefit of German Patent Application 10 2019 108 087.8, filed Mar. 28, 2019, the disclosure of which is incorporated herein by reference.

The invention relates to a process for isolating nucleic acids, such as DNA and RNA, using a non-alcoholic and non-chaotropic binding solution, and to the binding solutions and kits suitable for such a process.

BACKGROUND

The background of the invention is the development of a process and kit for isolating nucleic acids (DNA/RNA) from so-called "hard-to-lyse" sample materials (microorganisms, such as bacteria and fungi, insects, fatty tissues) and tissue samples by means of magnetic particles.

The isolation of nucleic acids (DNA/RNA) using chaotropic salts, alcohol, preferably ethanol and isopropanol, and a solid phase is still close to the prior art and has been employed repeatedly for many years. The binding of the nucleic acid, for example, to magnetic particles, is usually performed after the enzymatic lysis or mechanical disruption of the biological sample by adding a chaotropic salt and/or organic solvents, preferably ethanol or isopropanol, and optionally adding surfactants. Thus, EP-A-1502951, EP-A-1526176 and EP-A-1626085 (Agilent) describe methanol, ethanol, isopropanol and polyethylene glycol as organic binding enhancers in combination with a chaotropic salt solution for binding nucleic acids to a solid matrix. EP-A-1524317 (Roche) describes the use of acetone, acetylacetone, acetonitrile, dimethyl sulfoxide, diethyl ketone, methyl ethyl ketone, methyl propyl ketone, isobutyl methyl ketones, γ-butyrolactone, γ-valerolactone, propylene carbonate and N-methyl-2-pyrrolidone for binding nucleic acids to a mineral substrate. In this method, a mixture consisting of an aqueous buffer, salts in high concentrations and one of the above-mentioned organic components is employed. EP-A-2137309 (Stratagene) describes the use of sulfolane for isolating nucleic acids by contacting a sample containing nucleic acids, in the presence of salts and sulfolane, with a mineral substrate that absorbs at least one nucleic acid. EP-B-2322613 (Chomczynski) describes a method for isolating RNA from an RNA-containing sample by treating the sample with a monophasic, phenol-containing reagent and adding a water-soluble organic solvent to precipitate RNA, The organic solvent includes lower alcohols, polyalcohols, acetone, ethylene glycol diacetate, and methyl sulfoxide. US20170121702 (Axagarius) describes the use of an RNA-binding solution for binding RNA to a solid phase, consisting of at least one chaotropic agent and an organic solvent selected from the group of ethylene carbonate, ethylene glycol diacetate and 2-pyrrolidone, or a combination thereof. EP-A-1354036 (Life Technologies) describes a method for isolating nucleic acids by lysing a biological sample using a cationic surfactant and a protease, in which the binding to a solid matrix is effected by adding a non-ionic surfactant and a buffer with high salt concentrations.

Although alternative methods are known, they are still based on the addition of one of the above substances, e.g., isopropanol or chaotropic salt. To date, only a few methods have been known that totally eliminate the use of chaotropic salt and alcohol.

Because of the known drawbacks of reagent systems based on chaotropic salt/alcohol, the focus was on the provision of alternative reagent systems based on so-called "green solvents". The so-called "green solvents" are organic solvents that represent a non-hazardous/non-harmful alternative to toxic, irritant or hazardous substances, and are currently gaining more and more importance in various life science fields. Since the components employed or their combinations have been rarely mentioned to date in the context of DNA isolation, a patent application of the process is to be filed in order to protect the use of the specific binding solution in the context of DNA isolation.

SUMMARY OF THE INVENTION

It has now been found that the use of a binding solution consisting of at least one cyclic alkylene carbonate or an alkylene glycol diacetate and a non-ionic surfactant has advantageous effects on the binding of DNA to carboxylated magnetic particles. The specific binding reagent systems with "green solvent" components found are suitable for the nucleic acid isolation from a rather broad range of samples ("hard-to-lyse") in combination with various lysis methods (mechanical lysis and enzymatic lysis), wherein hazardous or irritating components, like chaotropic salt or alcohol, were essentially eliminated, not only in the binding step, but also in the remaining lysing, washing and insulation steps, so that these components are not part of the process and of the kit suitable therefor. Thus, the invention relates to:

(1) a process for isolating nucleic acids from a biological sample, comprising:
 (a) lysing the biological sample,
 (b) adding a binding solution comprising at least one organic solvent selected from cyclic $C_{2-4}$ alkylene carbonates, $C_{2-3}$ alkylene glycol diacetates, and derivatives thereof, and at least one non-ionic surfactant, and a nucleic acid-binding solid phase to the lysed sample, and separating the solid phase with the nucleic acids bound thereto,
 (c) washing the separated solid phase including the nucleic acids bound thereto once or several times with identical or different washing solutions, and
 (d) desorbing the nucleic acids from the solid phase by adding an aqueous elution buffer;

(2) a preferred embodiment of aspect (1), wherein said binding solution is a binding solution free of chaotropic salts;

(3) a binding solution for isolating nucleic acids from a biological sample, especially for a process according to aspect (1) or (2), comprising at least one organic solvent selected from cyclic $C_{2-4}$ alkylene carbonates, $C_{2-3}$ alkylene glycol diacetates, and derivatives thereof, and at least one non-ionic surfactant; and (4) a kit for isolating nucleic acids from a biological sample, especially for a process according to aspect (1) or (2), comprising a binding solution according to aspect (3), and optionally a nucleic acid-binding solid phase.

BRIEF DESCRIPTION OF THE DRAWINGS

The invention will now be described in greater detail with reference to the drawings wherein.

DETAILED DESCRIPTION OF THE INVENTION

Figure 1:
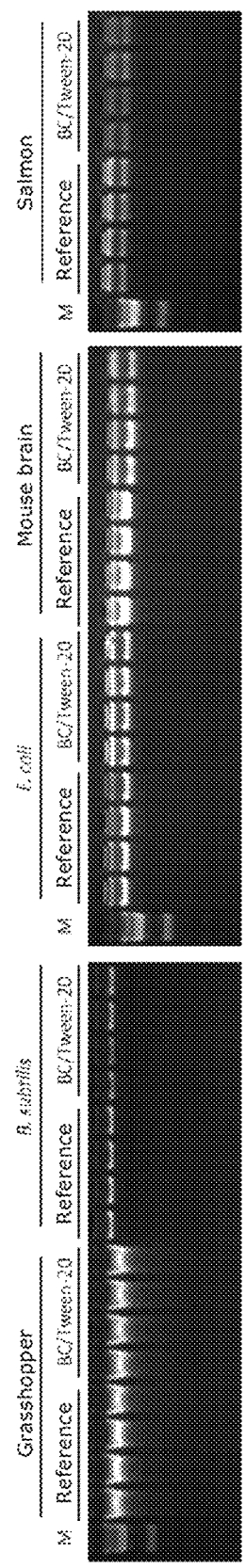
FIG. 1 shows TAE gels of DNA isolated as described in Example 4, Table 4.

Aspects (1) and (2) of the invention relate to a process for isolating nucleic acids from a biological sample. This includes the isolation of DNA and RNA as well as mixtures and derivatives thereof. The sample (e.g., cells, tissues) is either lysed by mechanical or enzymatic lysis using a lysing solution. Such lysing solutions preferably contain a low concentration of EDTA (≤500 mM) and/or another anionic surfactant (≤2.5% (w/v) SDS (sodium dodecylsulfate). Subsequently, the DNA is bound to the solid phase, in this case the magnetic particles, by adding magnetic particles and the binding solution. The solid phase is optionally washed by contacting it with one or more washing solutions, and subsequently eluted from the solid phase.

In the process of aspect (1) of the invention, the lysis may be effected by mechanical and/or enzymatic lysis using a lysing solution, wherein said lysing solution preferably contains low concentrations of EDTA and/or an anionic surfactant.

In a preferred embodiment of aspects (1) and (2) of the invention, not only is the binding solution in step (b) free of chaotropic salts, but so are also the lysing solution of step (a), the washing solution(s) of step (c), and/or the elution buffer of step (d), more preferably all the mentioned solutions and buffers are free of chaotropic salts.

"Free of chaotropic salts" as used in the present invention means that none of the compounds known to the skilled person as being chaotropic, such as thiocyanates, isothiocyanates, perchlorates, trichloroacetates, trifluoroacetates, iodides and/or guanidinium salts, such as, in particular, guanidinium chloride, guanidinium thiocyanate, guanidinium isothiocyanate, sodium thiocyanate, sodium iodide, sodium perchlorate, sodium trichloroacetate, sodium trifluoroacetate, urea, thiourea and phenol, that affect the secondary structure of nucleic acids, is present in the corresponding solution or the corresponding buffer. The "solutions" as used in the present invention need not necessarily contain (non-chaotropic) inorganic or organic salts and buffering substances, but they may be completely free therefrom, like in the case of the binding solution or some washing solutions. Thus, the "solutions" and the "elution buffer" as used in the present invention, unless stated otherwise, consist of aqueous solutions or aqueous alcoholic solutions (with ethanol or isopropanol as alcohol components, and an alcohol content of about 35 to about 100% (v/v)), admixed with suitable substances (e.g., inorganic or organic salts or buffering substances known to the skilled person, in sufficient amounts, i.e., up to about 3 M).

It is preferred that the cyclic $C_{2-4}$ alkylene carbonate in the binding solution is selected from butylene carbonate, propylene carbonate, ethylene carbonate, and derivatives thereof, the $C_{2-3}$ alkylene glycol diacetate is selected from ethylene glycol diacetate, propylene glycol diacetate, and derivatives thereof. "Derivatives" as used in the present invention are those of the above compounds in which one or more of the hydrogen atoms of the carbon chain(s) of the compounds are independently replaced by $C_{1-3}$ alkyl, $C_{1-3}$ alkoxy, hydroxy or halogen substituents. Preferably, the binding solution contains at least one compound selected from butylene carbonate (BC) (CAS 4437-85-8), propylene carbonate (PC) (CAS 108-32-7), ethylene carbonate (EC) (CAS 96-49-1), ethylene glycol diacetate (EGDA) (CAS 111-55-7) and propylene glycol diacetate (PGDA) (CAS 623-84-7), in which BC, PC, EC and EGDA are particularly preferred. Said at least one non-ionic surfactant is preferably selected from polyoxyethylene derivatives of sorbitan monolaureate, sorbitan monopalmitate and sorbitan monooleate, and polyoxyethylene derivatives, i.e. compounds of the Tween® series, and polyoxyethylene derivatives of fatty alcohols, i.e. compounds of the Brij® series, wherein polyoxyethylene (20) sorbitan monolaureate (Tween®-20; CAS 9005-64-5) is particularly preferred.

It is preferred that the ratio (v/v) of organic solvent (i.e., cyclic $C_{2-4}$ alkylene carbonate/$C_{2-3}$ alkylene glycol diacetate) to non-ionic surfactant, especially if the non-ionic surfactant is Tween®-20, is from about 80:20 to about 50:50, preferably from about 75:25 to about 55:45, more preferably about 70:30. It is preferred that the nucleic acid-binding solid phase in step (b) is magnetic carboxylated particles (carboxylated superparamagnetic particles with a particle size within a range of from about 0.5 to about 10 µm).

In step (b), the amount of binding solution added, expressed as a ratio to the volume of lysed sample, is from about 10:1 to about 1:10, preferably from about 3:1 to about 1:3, more preferably about 2:1 to about 1:1 (v/v) (binding solution/solution:lysed sample). The amount of solid phase added, expressed as a ratio to the volume of lysed sample, is at about 10:1 to about 50:1, preferably from about 20:1 to about 40:1, more preferably about 25:1 (v/v) (solid phase: lysed phase).

The washing solutions in step (c) include salt-containing aqueous solutions, preferably non-chaotropic ethanol-containing aqueous solutions, ethanol or ethanol-water mixtures (e.g., 80% ethanol, 20% water), with from about 0 to about 10% sodium acetate (w/v), 0-2% Tween 20 (w/v), 0-9% acetic acid (v/v). The volume of the respective washing solution is about 10 to about 50 times that of the solid phase (carboxylated superparamagnetic particles with a particle size within a range of from about 0.5 to about 10 µm).

The eluting solution of step (d) is preferably water or an alkaline low salt buffer (for example, an aqueous solution containing about 5 mM Tris/HCl, about pH 8.5). The volume of the eluting buffer is about once to about 20 times that of the solid phase.

The term "about" used herein allows a deviation from the respective base value of +/−10%.

In the following, a detailed sequence of the process according to the invention is outlined:

1. Lysing a biological sample by mechanical and/or enzymatic lysis using proteinase K and using a non-chaotropic lysing solution (consisting of from about 0.4 to about 2.5% SDS (w/v), and about 10 to about 400 mM EDTA).
2. Adding 320 µl of a binding solution consisting of a cyclic alkylene carbonate or alkylene glycol diacetate and a polysorbate in a ratio of about 70:30 (w/v), as well as magnetic carboxylated particles (carboxylated superparamagnetic particles with a particle size within a range of from about 0.5 to about 10 µm, for example, NucleoMag® B Beads from the kit NucleoMag® Tissue (MACHEREY-NAGEL, REF: 744300.1, 24 µl) as a solid phase for binding the nucleic acid.
3. The magnetic particles are optionally washed with one or more (chao-tropic) salt-containing ethanol-containing washing solutions (e.g., solution W1, W2, having a high content of chaotropic salt of about 5 to about 20% (w/v), or salt-containing aqueous ethanol-containing solutions, or ethanol-water mixtures (e.g., 80% ethanol, 20% water (v/v)) with 0 to 12.5% sodium acetate (w/v).

3. The magnetic particles are washed with an alcoholic washing solution (e.g., 80% ethanol, 20% water (v/v)).
4. The nucleic acid is released from the magnetic particles using water or a slightly alkaline low salt buffer (e.g., 5 mM Tris/HCl, pH 8.5).

The use of the above described binding solution is advantageous in comparison with other solution or reagent compositions, because it:
is hardly inflammable as compared to ethanol or isopropanol;
is less toxic or hazardous and thus more ecological;
reduces the use of chaotropic salts; and
enables the same or better yields and purities of isolated DNA, depending on the sample material.

In addition to said binding solution and nucleic acid-binding solid phase, the kit of aspect (4) may further contain one or more of the lysing solutions, washing solutions and eluting buffers as defined above.

The invention is explained in more detail using the following Examples. However, these do not in any way limit the claimed subject matter.

EXAMPLES

Materials and Methods

The following compounds and compositions were used in the following Examples: Butylene carbonate (CAS 4437-85-8) (>98.0%, TCI Chemicals), propylene carbonate (CAS 108-32-7) (99.7%, Sigma-Aldrich), ethylene carbonate (CAS 96-49-1) (>99.0%, TCI Chemicals), ethylene glycol diacetate (CAS 111-55-7) (99%, Sigma-Aldrich), propylene glycol diacetate (CAS 623-84-7) 99.7%, Sigma-Aldrich), Tween® 20 (Sigma-Aldrich), 40 (Sigma-Aldrich), 60 (Sigma-Aldrich) and 80 (Sigma-Aldrich), Brij® O10 and 58 (Sigma-Aldrich), sodium dodecylsulfate (SDS) (>98.5%, Sigma-Aldrich), sodium N-lauroylsarcosine (≥94%, Sigma-Aldrich), Triton X-100 (Sigma-Aldrich), Span® 40 (Sigma-Aldrich), 60 (Sigma-Aldrich), 65 (Sigma-Aldrich), 80 (Sigma-Aldrich), 83 (Sigma-Aldrich) and 85 (Sigma-Aldrich), ethylenediamine tetraacetic acid (EDTA, ≥99%, Carl Roth GmbH), Solution A (chaotropic salt and ethanol containing binding solution consisting of 50% ethanol (v/v) and 1.8 M sodium perchlorate) and Solution B (chaotropic salt and ethanol containing binding solution consisting of 2.4 M sodium perchlorate and 60% ethanol (v/v)); the solutions W1 and W2, consisting of 1.3 M sodium perchlorate and 35% ethanol (v/v), having a high content of chaotropic salt (5-20% (w/v)) and ethanol (20-35% (v/v)), the solution W3 consisting of 1.5 M sodium acetate and 50% ethanol (v/v), containing no chaotropic salt.

Description of the Standard Protocol

Unless stated otherwise, the experiments mentioned by way of example were performed according to the following protocol.

Enzymatic sample lysis: For each extraction, a specified amount of sample was incubated with a lysing solution (200 µl each) and proteinase K (25 µl each of a 30 mg/ml solution) with shaking at 56° C. for 1-16 h in a suitable reaction container to achieve lysis of the biological sample (hereinafter referred to as "lysate"). An optional subsequent centrifugation of the lysate, e.g., for 5 min at 5,600-6000×g, pelletizes undigested suspended solids.

Admixing with binding solution: To the clarified lysate, 320 µl of the respective binding solution and 24 µl of a magnetic bead suspension (carboxylated superparamagnetic particles with a particle size within a range of from 0.5 to 10 µm, for example, NucleoMag® B Beads from the kit NucleoMag® Tissue (MACHEREY-NAGEL, REF: 744300.1)) per extraction were added, and the lysate-bead binding solution mixture was mixed thoroughly by drawing it up and down the pipette. Optionally, other techniques, such as the use of a laboratory shaker or an automated magnetic particle processing device, may be used for the mixing.

Separating and washing: After the mixing is complete, the magnetic particles are separated off using a static or automated magnetic separator, so that either the supernatant containing lysate and binding solution can be separated by aspiration, or the magnetic particles can be separated by a mobile magnetic separator. The magnetic particles are subsequently resuspended in 800 µl of the respective washing solution or mixed thoroughly, for example, by drawing it up and down the pipette, shaking or other techniques. After the mixing is complete, there is another separation of the magnetic particles from the respective washing buffer by one of the techniques described above. In the further course, two more washing steps are performed with the respective washing solutions (800 µl each) according to the above described principle, wherein an 80% ethanol-water mixture is used as a washing solution in the third washing step.

Elution: After a drying step for 5 to 10 min at room temperature, the DNA was released from the magnetic particles by adding 100 µl of eluting buffer (5 mM Tris/HCl, pH 8.5), and separated off by means of a magnetic separator, as described above.

Example 1

Per extraction, 20 mg of an animal tissue (roe deer liver for #1-17; pig kidney #18-19) was lysed using an SDS-containing lysing solution (200 µl per sample; 1% SDS (w/v), 100 mM EDTA, 10 mM Tris) and using proteinase K (about 30 mg/ml) with shaking at 56° C. over night. Subsequently, 320 µl of the respective binding solution and 24 µl (carboxylated superparamagnetic particles with a particle size within a range of from 0.5 to 10 µm) of NucleoMag® B Beads per sample were added. The following Table 1 shows relative and absolute yields of DNA as a function of the different binding solution compositions (v/v) in comparison with reference buffers.

TABLE 1

| # | Substance A | Substance B | DNA yield [µg] | Relative yield [%] |
|---|---|---|---|---|
| 1 | BC 100% | — | 1.4 | 4.50 |
| 2 | BC 80% | Tween ®20 20% | 2.0 | 6.43 |
| 3 | BC 70% | Tween ®20 30% | 14.3 | 45.98 |
| 4 | BC 60% | Tween ®20 40% | 26.2 | 84.24 |
| 5 | PC 100% | — | 1.3 | 4.18 |
| 6 | PC 80% | Tween ®20 20% | 2.6 | 8.36 |
| 7 | PC 70% | Tween ®20 30% | 28.8 | 92.60 |
| 8 | PC 60% | Tween ®20 40% | 28.1 | 90.35 |
| 9 | EC 100% | | not measurable | — |
| 10 | EC 80% | Tween ®20 20% | not measurable | — |
| 11 | EC 70% | Tween ®20 30% | 34.0 | 109.32 |
| 12 | EC 60% | Tween ®20 40% | 35.2 | 113.18 |
| 13 | EGDA 100% | — | 1.5 | 4.82 |
| 14 | EGDA 80% | Tween ®20 20% | 26.8 | 86.17 |
| 15 | EGDA 70% | Tween ®20 30% | 29.4 | 94.53 |
| 16 | EGDA 60% | Tween ®20 40% | 31.8 | 102.25 |

TABLE 1-continued

| # | Substance A | Substance B | DNA yield [μg] | Relative yield [%] |
|---|---|---|---|---|
| 17 | | Solution B | 31.1 | 100 |
| 18 | — | Tween ®20 35% | 0.4 | 6.78 |
| 19 | | Solution B | 5.9 | 100 |
| 20 | PGDA 100% | — | 0.7 | 3.77 |
| 21 | PGDA 80% | Tween ®20 20% | 1.3 | 67.63 |
| 22 | PGDA 70% | Tween ®20 30% | 16.0 | 84.89 |
| 23 | PGDA 60% | Tween ®20 40% | 14.4 | 76.46 |
| 24 | | Solution A | 18.9 | 100 |

The mixture of lysate, beads and binding solution was subsequently processed automatically according to the specifications in the above described standard protocol, wherein the magnetic particles were washed twice with 800 μl each of washing solution W1, and with 800 μl each of 80% ethanol. After a drying step, the DNA was released from the magnetic particles by adding by adding 100 μl of eluting buffer (5 mM Tris/HCl, pH 8.5), and separated off. The DNA yield was determined by UV spectrometry and expressed in relation to the reference solution, Solution B (#17/#19) or Solution A (#24) (binding solution containing chaotropic salts and ethanol).

From the data, it can be seen that mixtures of BC, PC, EC or EGDA and Tween®20 can be employed during DNA isolation as an alternative binding solution for binding solutions containing chaotropic salts and alcohol.

Example 2

The DNA isolation was from mechanically lysed fatty sample material. The sample material was lysed with 140 μl of an EDTA-containing aqueous solution (500 mM EDTA) by mechanical lysis using 5×3 mm steel balls in a 2 ml screw cap vessel for 1 min at 10 Hz, followed by 1 min at 20 Hz, in a vibration mill. In addition, the washing solution W2 was replaced by the washing solution W3 consisting of 50% ethanol and 50% of a 3 M sodium acetate solution in order to avoid the use of chaotropic salt in the washing solutions. The following Table 2 shows the relative and absolute yields of DNA as a function of the different compositions of the binding solutions, which were used at a ratio of 70:30 (v/v; see below). A kit based on chaotropic salts and ethanol was used as a reference.

TABLE 2

| Extraction | BC/ Tween ®20 | PC/ Tween ®20 | EC/ Tween ®20 | EGDA/ Tween ®20 | Reference: NucleoSpin ® Lipid Tissue |
|---|---|---|---|---|---|
| 1 | 3.69 | 2.5 | 0.38 | 3.96 | 3.4 |
| 2 | 2.22 | 3.81 | 0.35 | 2.63 | 3.9 |
| 3 | 4.31 | 2.13 | 0.36 | 2.42 | 4.1 |
| 4 | 4.03 | 2.79 | 0.42 | 3.5 | 6.8 |
| Mean value | 3.6 | 2.8 | 0.4 | 3.1 | 4.6 |

From the data, it can be seen that mixtures of a cyclic alkylene carbonate or ethylene glycol diacetate and a polysorbate can be employed during DNA isolation as an alternative binding solution for binding solutions containing chaotropic salts and alcohol.

Example 3

Per extraction, 20 mg of an animal tissue (roe deer liver for #1-17; pig kidney #18-19) was processed using an SDS- and EDTA-containing lysing solution (200 μl per sample; 1% SDS (w/v), 100 mM EDTA, 10 mM Tris) and using proteinase K (30 mg/ml) according to the specifications in the above described standard protocol. Subsequently, 320 μl of the respective binding solution and 24 μl of NucleoMag® B Beads (carboxylated superparamagnetic particles with a particle size within a range of from 0.5 to 10 μm) per sample were added. The following binding solution compositions were used at a ratio of 70:30 (v/v). The further processing was effected according to the statements made under Example 1.

The DNA yield was determined by UV spectrometry and expressed in relation to the reference solution, Solution A (#7). The following Table 3 shows relative and absolute yields of DNA as a function of the different binding solution compositions.

TABLE 3

| # | Substance A | Substance B | DNA yield [μg] | Relative yield [%] |
|---|---|---|---|---|
| 1 | BC | Tween ®20 | 24.6 | 113.16 |
| 2 | BC | Tween ®40 | 20.4 | 94.12 |
| 3 | BC | N-Lauroylsarcosine | 1.4 | 6.2 |
| 4 | BC | Triton X-100 | 1.5 | 6.92 |
| 5 | BC | SDS (10% stock solution) | 1.0 | 4.39 |
| 6 | BC | Brij ® 58 | 0.7 | 3.31 |
| 7 | Solution A (Reference) | | 21.7 | |
| 8 | BC | Tween ®80 | 32.4 | 134.89% |
| 9 | BC | Span ® 40 | 2.8 | 11.61 |
| 10 | BC | Span ® 60 | 1.9 | 7.98 |
| 11 | BC | Span ® 65 | 2.6 | 10.81 |
| 12 | BC | Span ® 80 | 9.7 | 40.13 |
| 13 | BC | Span ® 83 | 8.6 | 35.72 |
| 14 | BC | Span ® 85 | 6.6 | 27.42 |
| 15 | BC | Brij ® O10 | 13.9 | 57.80 |
| 16 | Solution A (Reference) | | 24.1 | |

From the data, it can be seen that mixtures of BC and a polysorbate can be employed during DNA isolation as an alternative binding solution for binding solutions containing chaotropic salts and alcohol, and are advantageous.

Example 4

In order to demonstrate the versatility of the method, DNA was isolated from difficult, so-called "hard-to-lyse" sample materials from different organisms. In addition to insects and microorganisms, these include particularly fatty tissues, such as brain or fish samples. A known problem is the turbidity of the eluates from insufficient removal of contaminants. The following sample materials and amounts were used:

grasshopper 40 mg
*Bacillus subtilis* about $1\times10^9$ cells
*Escherichia coli* about $1\times10^9$ cells mouse brain 20 mg salmon 20 mg The corresponding sample material was lysed using 200 µl of an SDS- and EDTA-containing lysing solution (1% SDS (w/v), 100 mM EDTA, 10 mM Tris) and 25 µl of proteinase K (about 30 mg/ml) according to the specifications of the procedure described in Example 1 with shaking over night at 56° C. Subsequently, after the addition of 20 µl RNase A (20 mg/ml), the lysates were incubated for 5 min at room temperature, and clarified by centrifugation (4500× g, 20 min). Per sample, 225 µl of the clarified lysate was transferred and processed according to the specifications of the procedure described in Example 1. A mixture of BC/Tween®20 and EGDA/Tween®20 at a ratio of 70 to 30 (v/v) was used as a binding solution. The binding solution, Solution A, was used as a reference.

The quantity and quality of the isolated DNA were analyzed by agarose gel electrophoresis and a fluorometric quantification method. The following Table 4 shows absolute DNA yields (mean value) as compared to the mean value of the reference (buffer A).

TABLE 4

| Sample material | Binding solution | DNA yield [µg] | A260/ A280 | A260/ A230 | Turbidity of the eluates |
|---|---|---|---|---|---|
| Grasshopper | BC/Tween ®20 | 11.9 | 1.7 | 1.9 | — |
|  | Solution A | 15.5 | 1.4 | 1.1 | turbid |
| Bacillus subtilis | BC/Tween ®20 | 3.7 | 1.5 | 1.0 | — |
|  | Solution A | 1.3 | 1.5 | 1.1 | — |
| Escherichia coli | BC/Tween ®20 | 4.0 | 1.7 | 1.3 | — |
|  | Solution A | 3.4 | 1.5 | 0.8 | — |
| Mouse brain | BC/Tween ®20 | 3.7 | 1.7 | 1.4 | — |
|  | Solution A | 8.2 | 1.3 | 0.9 | turbid |
| Salmon | BC/Tween ®20 | 0.7 | 1.5 | 0.8 | — |
|  | Solution A | 1.7 | 1.3 | 0.7 | turbid |

FIG. 1 shows TAE gels of the isolated DNA. Per sample, 3 µl of the eluate was applied to a 1% TAE gel (M: Lambda Hind III marker).

The following Table 5 shows absolute DNA yields (mean value) as compared to the mean value of the reference (buffer A).

TABLE 5

| Sample material | Binding solution | DNA yield [µg] | A260/ A280 | A260/ A230 | Turbidity of the eluates |
|---|---|---|---|---|---|
| Grasshopper | EGDA/Tween ®20 | 29.5 | 1.7 | 1.9 | — |
|  | Solution A | 24.6 | 1.4 | 1.1 | turbid |
| Bacillus subtilis | EGDA/Tween ®20 | 2.6 | 1.6 | 1.1 | — |
|  | Solution A | 2.4 | 1.6 | 1.2 | — |
| Escherichia coli | EGDA/Tween ®20 | 9.2 | 1.5 | 0.9 | — |
|  | Solution A | 10.1 | 1.5 | 0.9 | — |
| Mouse brain | EGDA/Tween ®20 | 17.2 | 1.7 | 1.5 | — |
|  | Solution A | 10.9 | 1.3 | 0.9 | turbid |
| Salmon | EGDA/Tween ®20 | 2.2 | 1.6 | 1.1 | — |
|  | Solution A | 2.9 | 1.3 | 0.7 | turbid |

Figure 2:
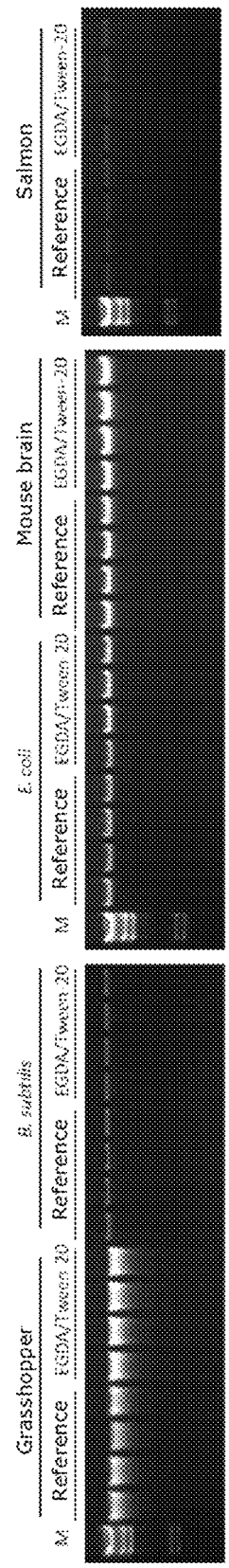
FIG. 2 shows TAE gels of DNA isolated as described in Example 4, Table 5.

FIG. 2 shows TAE gels of the isolated DNA. Per sample, 1 µl of the eluate was applied to a 1% TAE gel (M: Lambda Hind III marker).

From the data represented here, it can be seen that a binding solution consisting of BC or EGDA and a polysorbate (Tween®20) proves advantageous in terms of purity and yield of the isolated DNA.

Example 5

Per sample, 20 mg of roe deer liver was lysed using an SDS-containing lysing solution (1% SDS (w/v), 100 mM EDTA, 10 mM Tris) and 25 µl proteinase K (about 30 mg/ml) according to the specifications in the above described standard protocol. Subsequently, 320 µl of the respective binding solution and 30 µl of the respective magnetic particles, silanized (NucleoMag® P Beads) or carboxylated (NucleoMag® B Beads) (superparamagnetic particles with a particle size within a range of from 0.5 to 10 µm), were added, and incubated with shaking. The magnetic particles were subsequently processed according to the specifications in Example 1. The following Table 6 shows absolute yields of DNA using different binding solutions as a function of the solid phase.

TABLE 6

| # | Substance A | Substance B | Solid phase | DNA yield [µg] |
|---|---|---|---|---|
| 1 | Butylene carbonate | Tween ®20 35% | NucleoMag ® P Beads | 0.6 |
| 2 | 65% |  | NucleoMag ® B Beads | 7.4 |
| 3 | Propylene carbonate | Tween ®20 35% | NucleoMag ® P Beads | 1.0 |
| 4 | 65% |  | NucleoMag ® B Beads | 9.7 |
| 5 | Ethylene carbonate | Tween ®20 35% | NucleoMag ® P Beads | 4.9 |
| 6 | 65% |  | NucleoMag ® B Beads | 11.6 |
| 7 | Ethylene glycol | Tween ®20 35% | NucleoMag ® P Beads | 0.5 |
| 8 | diacetate 65% |  | NucleoMag ® B Beads | 11.2 |
| 9 | Solution B |  | NucleoMag ® P Beads | 0.6 |
| 10 |  |  | NucleoMag ® B Beads | 5.9 |

The data show that the efficiency of the binding strongly depends on the kind of surface of the solid phase. In addition, it can be seen that a higher yield of DNA can be achieved using the binding solution compositions stated here as compared to the reference buffer.

Per extraction, 30 mg of an animal tissue (pig kidney) was lysed using an SDS- and EDTA-containing lysing solution (200 µl per extraction; 1% SDS (w/v), 100 mM EDTA, 10 mM Tris) and using proteinase K (25 µl of a 30 mg/ml solution per extraction) over night according to the specifications in the above described standard protocol. Subsequently, 320 µl of an EGDA/Tween®20 binding solution at a ratio of 70:30 (v/v) and 24 µl of NucleoMag® B Beads (carboxylated superparamagnetic particles with a particle size within a range of from 0.5 to 10 µm) per sample were added. As the washing solution, either a non-chaotropic combination of washing solutions (W3/W3/80% EtOH) or chaotropic combinations of washing solutions (W2/W2/80% EtOH or W1/W2/80% EtOH) were employed. The further processing was effected according to the statements made under Example 1.

The DNA yield and purity was determined by UV spectrometry and expressed in relation to the reference solution, Solution A (#7). The following Table 7 shows absolute DNA yields in comparison with the mean value of the reference (buffer A).

TABLE 7

| Binding solution | Combinations of washing solutions | DNA yield [µg] | A260/A280 | A260/A230 | Turbidity of the eluates |
|---|---|---|---|---|---|
| EGDA/ | W3/W3/80% EtOH | 23.8 | 1.9 | 2.3 | — |
| Tween ®-20 | W2/W2/80% EtOH | 22.4 | 1.9 | 2.3 | — |
| Solution A | W1/W2/80% EtOH | 19.8 | 1.8 | 2.2 | — |

From the data represented here, it can be seen that the above described binding solution may also be used with non-chaotropic washing solutions, and proves advantageous in terms of purity and yield of the isolated DNA.

Example 7

Per extraction, 20 mg of an animal tissue (pig kidney) was lysed using an SDS- and EDTA-containing lysing solution (200 µl per extraction; 1% SDS (w/v), 100 mM EDTA, 10 mM Tris) and using proteinase K (25 µl of a 30 mg/ml solution per extraction) over night according to the specifications in the above described standard protocol. Subsequently, 24 µl of NucleoMag® B Beads (carboxylated superparamagnetic particles with a particle size within a range of from 0.5 to 10 µm) and 320 µl of an EGDA/Tween®20 binding solution at a ratio of 70:30 (v/v) or of a mixture of binding solutions consisting of EGDA and a 1.8 M solution of a chaotropic salt (guanidinium chloride (GuHCl); guanidinium thiocyanate (GITC); sodium perchlorate ($NaClO_4$)) per sample were added. The further processing was effected according to the statements made under Example 1.

The DNA yield and purity was determined by UV spectrometry and expressed in relation to the reference solution, Solution A, or the binding solution EGDA/Tween®20 (70/30 (v/v)).

Figure 3:
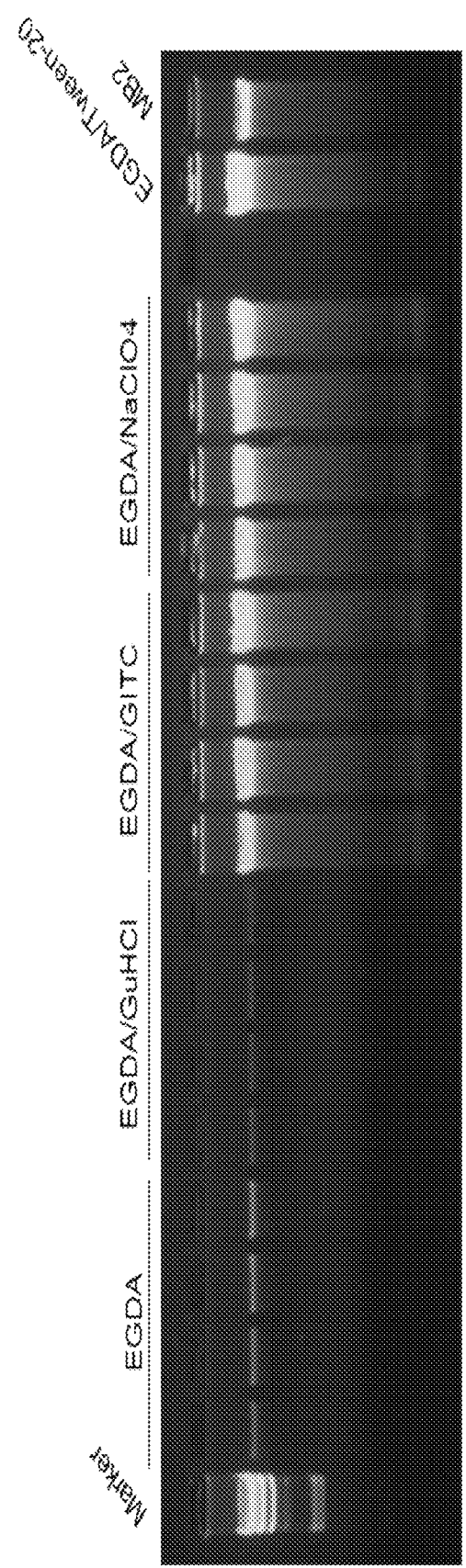
FIG. 3 shows TAE gels of DNA isolated as described in Example 7.

FIG. 3 shows TAE gels of the isolated DNA. Per sample, 1 µl of the eluate was applied to a 1% TAE gel (M: Lambda Hind III marker).

The above data show that the binding solution described herein is equivalent to a mixture of binding solutions containing chaotropic salts.

The invention claimed is:

1. A process for isolating nucleic acids from a biological sample, comprising:
   (a) lysing the biological sample,
   (b) adding a binding solution being free of chaotropic salts and comprising at least one organic solvent selected from the group consisting of cyclic $C_{2-4}$ alkylene carbonates, $C_{2-3}$ alkylene glycol diacetates, and derivatives thereof, at least one non-ionic surfactant, and nucleic acid-binding carboxylated magnetic particles as a nucleic acid-binding solid phase to the lysed sample, and separating the solid phase with the nucleic acids directly bound thereto,
   (c) washing the separated solid phase including the nucleic acids bound thereto once or several times with identical or different washing solutions, and
   (d) desorbing the nucleic acids from the solid phase by adding an aqueous elution buffer.

2. The process according to claim 1, wherein said lysis is effected by mechanical and/or enzymatic lysis using a lysing solution, wherein said lysing solution optionally contains low concentrations of EDTA and/or an anionic surfactant.

3. The process according to claim 1, wherein, not only said binding solution in step (b), but also the lysing solution of step (a), the washing solution(s) of step (c), and/or the elution buffer of step (d), are free of chaotropic salts.

4. The process according to claim 1, wherein, in the binding solution, the cyclic $C_{2-4}$ alkylene carbonate is selected from the group consisting of butylene carbonate, propylene carbonate, ethylene carbonate, and derivatives thereof, and the $C_{2-3}$ alkylene glycol diacetate is selected from the group consisting of ethylene glycol diacetate, propylene glycol diacetate, and derivatives thereof.

5. The process according to claim 4, wherein the binding solution contains at least one compound selected from the group consisting of butylene carbonate, propylene carbonate, ethylene carbonate, and ethylene glycol diacetate.

6. The process according to claim 1, wherein, in the binding solution, said at least one non-ionic surfactant is selected from the group consisting of polyoxyethylene derivatives of sorbitan monolaureate, sorbitan monopalmitate and sorbitan monooleate, and polyoxyethylene derivatives of fatty alcohols.

7. The process according to claim 6, wherein said at least one non-ionic surfactant is polyoxyethylene(20) sorbitan monolaureate.

8. The process according to claim 1, wherein, in the binding solution, the ratio (v/v) of organic solvent to non-ionic surfactant is from 80:20 to 50:50.

9. The process according to claim 8, wherein the ratio (v/v) of organic solvent to non-ionic surfactant is from about 75:25 to about 55:45 or is about 70:30.

10. The process according to claim 1, wherein, in step (b),
   (i) the amount of binding solution added as a ratio to the volume of lysed sample is from about 10:1 to about 1:10 (v/v); and
   (ii) the amount of solid phase added as a ratio to the volume of lysed sample is from about 10:1 to about 50:1 (v/v).

11. The process according to claim 10, wherein the amount of binding solution added as a ratio to the volume of lysed sample is from about 3:1 to about 1:3 (v/v), or is about 2:1 to about 1:1 (v/v).

12. The process according to claim 10, wherein the amount of solid phase added as a ratio to the volume of lysed sample is from about 20:1 to about 40:1 (v/v), or is about 25:1 (v/v).

13. The process according to claim 1, wherein the washing solutions in step (c) are selected from the group consisting of salt-containing aqueous solutions, salt-containing and ethanol-containing aqueous solutions, and salt-containing ethanolic solutions.

14. The process according to claim 13, wherein the washing solutions are selected from the group consisting of non-chaotropic aqueous solutions, non-chaotropic ethanol-water mixtures and ethanol.

15. The process according claims 1, wherein the eluting solution of step (d) is an alkaline low salt buffer.

16. A binding solution for isolating nucleic acids from a biological sample, said binding solution being free of chaotropic salts and said binding solution comprising at least one organic solvent selected from the group consisting of cyclic $C_{2-4}$ alkylene carbonates, $C_{2-3}$ alkylene glycol diacetates, and derivatives thereof, at least one non-ionic surfactant, and nucleic acid-direct-binding carboxylated magnetic particles as a nucleic acid-binding solid phase.

17. The binding solution according to claim 16, which is a binding solution free of chaotropic salts.

18. A kit for isolating nucleic acids from a biological sample, comprising a binding solution that is free of chaotropic salts and said binding solution comprising at least one organic solvent selected from the group consisting of cyclic $C_{2-4}$ alkylene carbonates, $C_{2-3}$ alkylene glycol diacetates, and derivatives thereof, at least one non-ionic surfactant, and nucleic acid-direct-binding carboxylated magnetic particles as a nucleic acid-binding solid phase.

19. The kit according to claim 18, which further comprises one or more of lysing solutions, washing solutions and eluting buffers.

20. The process according to claim 1, wherein in step (b) the carboxylated magnetic particles are carboxylated superparamagnetic particles with a particle size within a range from about 0.5 to about 10 µm.

21. The binding solution according to claim 16, wherein the carboxylated magnetic particles are carboxylated superparamagnetic particles with a particle size within a range from about 0.5 to about 10 µm.

22. The kit according to claim 18, wherein the carboxylated magnetic particles are carboxylated superparamagnetic particles with a particle size within a range from about 0.5 to about 10 µm.

* * * * *